United States Patent
Lucke et al.

(10) Patent No.: US 6,609,900 B2
(45) Date of Patent: Aug. 26, 2003

(54) DYNAMIC BRAKE WITH BACKLASH CONTROL FOR PERISTALTIC PUMP

(75) Inventors: Lori E. Lucke, Eagan, MN (US); David Danielson, Chelsea, MN (US); Richard A. Griewski, Howell, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 0 days.

(21) Appl. No.: 10/078,679

(22) Filed: Feb. 21, 2002

(65) Prior Publication Data

US 2002/0127115 A1 Sep. 12, 2002

(51) Int. Cl.[7] ............... F04B 43/08; F04B 49/00; F04B 49/06
(52) U.S. Cl. ............... 417/474; 417/22; 417/42; 417/44.1
(58) Field of Search ............... 417/474, 22, 42, 417/44.1

(56) References Cited

U.S. PATENT DOCUMENTS

| 4,705,668 A | * | 11/1987 | Kaltenbach et al. ........... 422/82 |
| 4,781,548 A | * | 11/1988 | Alderson et al. ............ 417/474 |
| 4,910,682 A | * | 3/1990 | Wolff et al. ................ 702/46 |
| 5,657,000 A | * | 8/1997 | Ellingboe .................. 340/608 |
| 5,996,650 A | * | 12/1999 | Phallen et al. ............... 141/83 |

* cited by examiner

Primary Examiner—Charles G. Freay
Assistant Examiner—Timothy P. Solak
(74) Attorney, Agent, or Firm—Burns, Doane, Swecker & Mathis, LLP

(57) ABSTRACT

The present invention involves a dynamic brake for use in a peristaltic (i.e., roller) pump. The dynamic brake avoids backlash, due to counter rotation. In addition, it does not preclude the option of hand operating the roller pump. This is achieved by initiating the braking operation after the roller pump set-point has been set to zero and only after the roller pump has decelerated below a predefined speed (e.g., 20 rpm). In addition, the braking operation is activated for only a very brief period of time (i.e., a period of time required for the pressure in the roller pump fluid conduit to subside).

10 Claims, 5 Drawing Sheets

DYNAMIC BRAKE WITH BACKLASH CONTROL FOR PERISTALTIC PUMP

TECHNICAL FIELD

The present invention is directed to a dynamic brake with backlash control, and more particularly, to a dynamic brake with backlash control for use with a peristaltic pump.

BACKGROUND OF THE INVENTION

Peristaltic pumps, also referred to as roller pumps, are commonly utilized in medical applications. For instance, such pumps are often employed during cardiovascular surgery to facilitate circulation of blood between a patient and a heart-lung machine. Other common medical uses are the transfer of blood between a patient and a kidney dialyzer, and intravenous feeding of IV solutions. Generally, peristaltic pumps are simply structured, generate a constant flow, and employ disposable tubes as a member for fluid transfer.

Peristaltic pumps are relatively simple in construction and typically include a housing having rollers which progressively compress a flexible tube at spaced intervals against an arcuate surface or raceway so as to flatten or locally reduce the cross-sectional area of the tube. In this manner, fluid leading to the flexible tube is continuously forced through the flexible tube by one or another of the rollers as it proceeds along the flexible tube over the arcuate surface or raceway.

A conventional roller pump 10, as shown in FIG. 1, comprises a drive mechanism 14 furnished with a drive shaft 12, a rotating shaft 16 which rotates according to the rotation of drive shaft 12, and a hollow pump head 20 fixed to a housing 18 to which drive mechanism 14 is attached. This pump head 20 integrally incorporates a bearing block 24 through which rotating shaft 16 is inserted and rotatably supported by a pair of bearings 22 and a stator 26 arranged on the upper portion of bearing block 24. On the upper surface of stator 26 is formed a recess 28 through which the upper end of rotating shaft 16 is protruded. While this recess 28 is radially and outwardly spaced at a certain distance from the outer circumferential surface of rotating shaft 16, its inner circumferential surface 28a is coaxial with rotating shaft 16.

A rotor assembly 30 is attached to the upper portion of rotating shaft 16 in such a way as to be placed inside recess 28 of stator 26 and to stay opposite the inner circumferential surface 28a thereof. This rotor 30 is fixed to rotating shaft 16 through a bolt 32, and is so constructed as to integrally rotate along with rotating shaft 16. On the outer circumferential surface of rotor 30, at least one roller 34 is arranged so as to rotate about its own axes. A tube 36 which is filled with blood or other fluid material is placed between rotor 30 and stator 26. Tube 36 is clamped between respective rollers 34, which are attached to rotor 30, and inner circumferential surface 28a of stator 26, thereby maintaining tube 36 in a closed state at the point at which it is clamped.

Thus, in a conventional roller pump 10, rotor 30 is rotated by the rotational motion of rotating shaft 16 driven by drive mechanism 14, and the clamped portions of tube 36 move according to the revolution of rollers 34 around rotating shaft 16. Therefore, fluid inside tube 36 is transferred according to the revolution of rollers 34. The rate of rotation of the rotating shaft 16 and hence the rollers 34 is normally adjustable so that the pumping rate of the fluid within tube 36 can be adjusted. However, the pumping rate can also be adjusted by adjusting the degree to which the rollers compress the flexible tube. This can be done in peristaltic pump assemblies by providing an adjustment mechanism for adjusting the distance between the axes of the rollers and hence the distance between the roller surface and the inner circumferential surface 28a of stator 26. Another important reason for peristaltic pumps to be adjustable in this fashion is that the compressibility, size, and other qualities of the flexible tube can vary considerably.

Referring also to FIG. 2, the operation of a typical roller pump 10 is illustrated. Although roller pumps are typically capable of rotating in either direction, the solid arrow in FIG. 2 indicates that roller pump 10 is rotating in a clockwise direction to force blood through the tube or fluid conduit 36. Generally, the roller pump 10 continues to rotate until the motor drive circuitry (not shown) is disabled. When this occurs, the roller pump coasts to a gradual stop. After the roller pump has come to a complete stop, it is desirable if the rollers 34a, 34b, 34c are left free to move (i.e., rotate). This is desirable because it allows the roller pump to be hand-operated (i.e., hand-cranked), if that should become necessary.

However, when the rollers are left free to move, it is common for the roller pump to experience some recoil, that is, some amount of counter rotation (e.g., 20 degrees of counter rotation) immediately after the rollers reach zero RPM. In FIG. 2, the counter rotation is depicted by the "broken line" arrow. The recoil, referred to herein as backlash, is due to the fact that the rollers are left free to move, and because there is a certain amount of counter pressure in the fluid conduit which opposes the normal rotation (e.g., clockwise rotation) of the roller pump. Backlash may cause air to be introduced into the conduit. This highly undesirable condition may lead to an air embolism or even death of the patient.

Some roller pumps employ a continuously applied brake to prevent backlash due to counter rotation. A continuously applied brake is an electrical or mechanical brake which is continuously applied to stop the motor within the pump. The brake is never removed until it is deemed necessary for the pump to begin moving the rollers again, so as to move fluid in the pump. These pumps may activate the continuously applied brake as soon as the motor drive circuitry receives a signal to stop the pump. While the continuously applied brake does, to some extent, prevent backlash, it also prevents the rollers from freely moving after the rollers have stopped rotating. In this instance, the continuously applied brake would preclude the option of hand operating the roller pump.

Accordingly, there is a need in the art for an improved braking feature for a roller pump, which substantially reduces the occurrence of backlash yet allows the roller pump to be hand operated if necessary.

SUMMARY OF THE INVENTION

It is an object of the present invention to provide an intelligent, momentary dynamic brake for use in a roller pump to prevent backlash.

It is also an object of the present invention to provide intelligent, momentary dynamic braking in a roller pump without jeopardizing the ability to hand operate the pump after the rollers have stopped rotating.

In a first embodiment of the present invention, the aforementioned and other objects are achieved by a roller pump that includes means for activating a dynamic brake when the roller pump decelerates below a predefined pump speed. The pump also includes means for deactivating the dynamic brake when pressure in the fluid conduit of the roller pump subsides.

In another embodiment of the present invention, the aforementioned and other objects are achieved by a method for preventing backlash in a roller pump. The method involves determining whether the speed of the roller pump is less than a predefined roller pump speed threshold. When it has been determined that the speed of the roller pump is less than the predefined roller pump speed threshold, a dynamic brake is activated. Then, after a predefined period of time has elapsed, the dynamic brake is deactivated.

BRIEF DESCRIPTION OF THE FIGURES

These, and other, objects, features and advantages of the present invention will become more readily apparent to those skilled in the art upon reading the following detailed description, in conjunction with the appended drawings, in which.

DETAILED DESCRIPTION OF THE INVENTION

Figure 1:
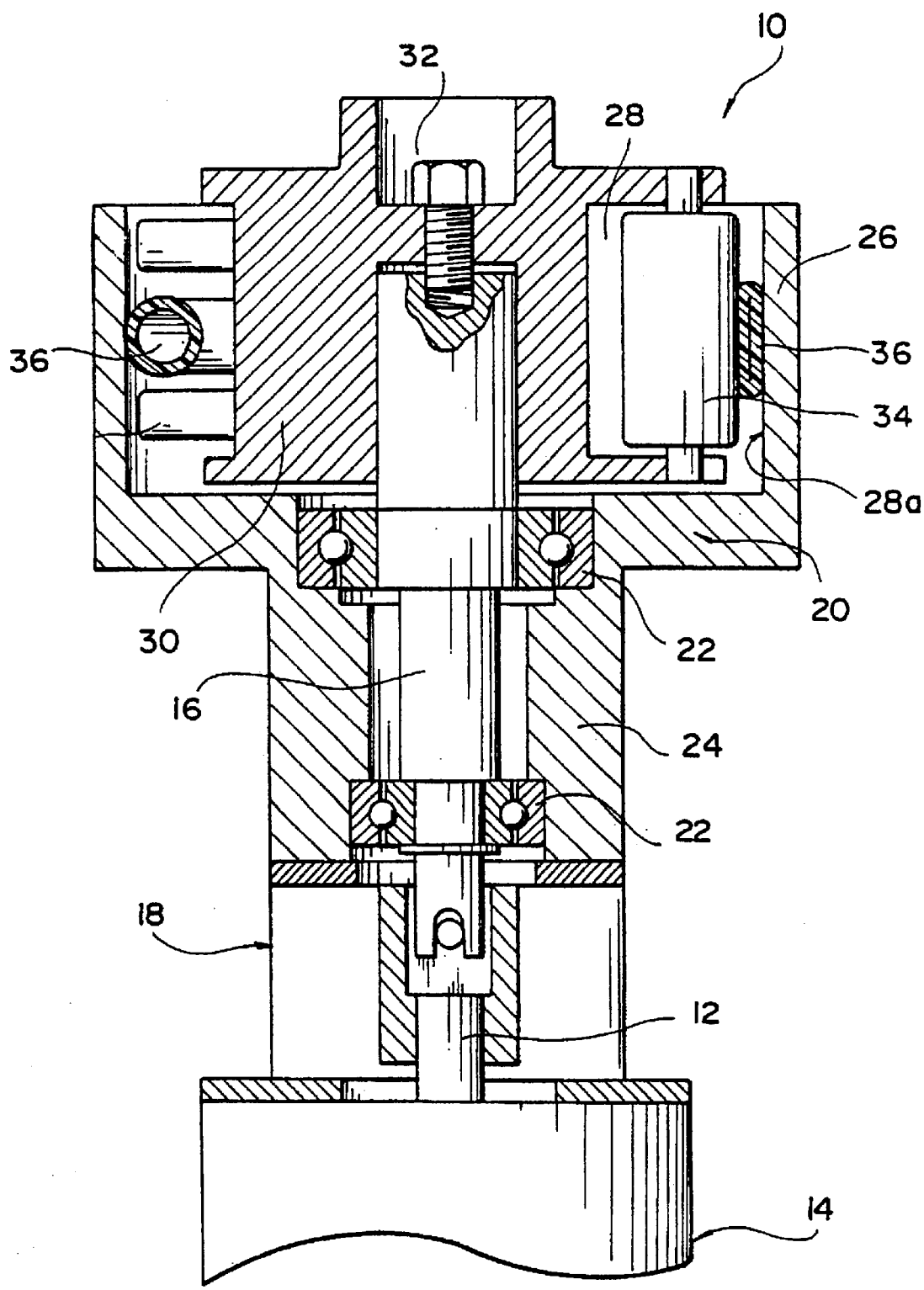
FIG. 1 is a cross-sectional view of a peristaltic pump as known in the prior art.
Figure 2:
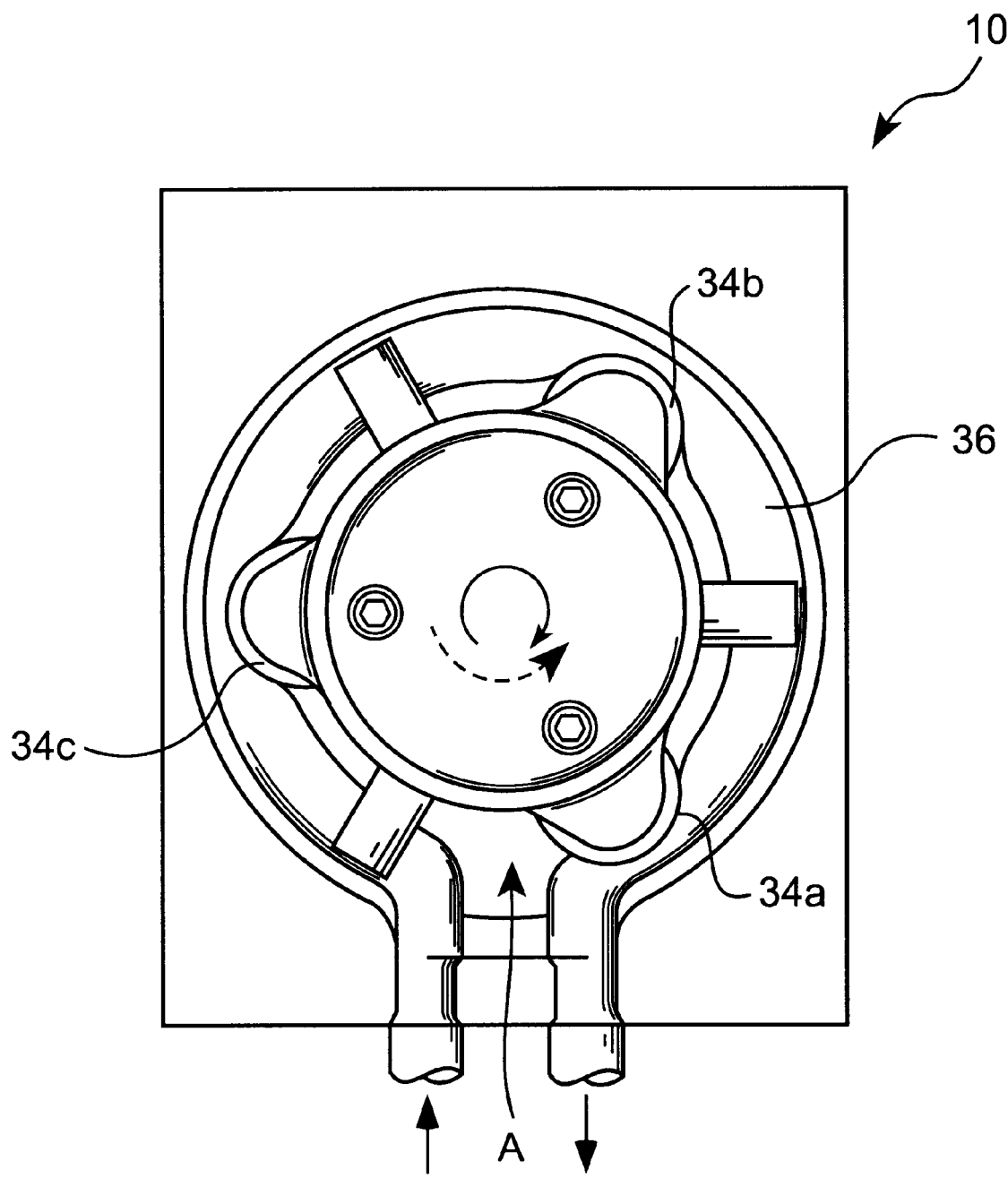
FIG. 2 is a top plan view of a peristaltic pump as known in the art.
Figure 3:
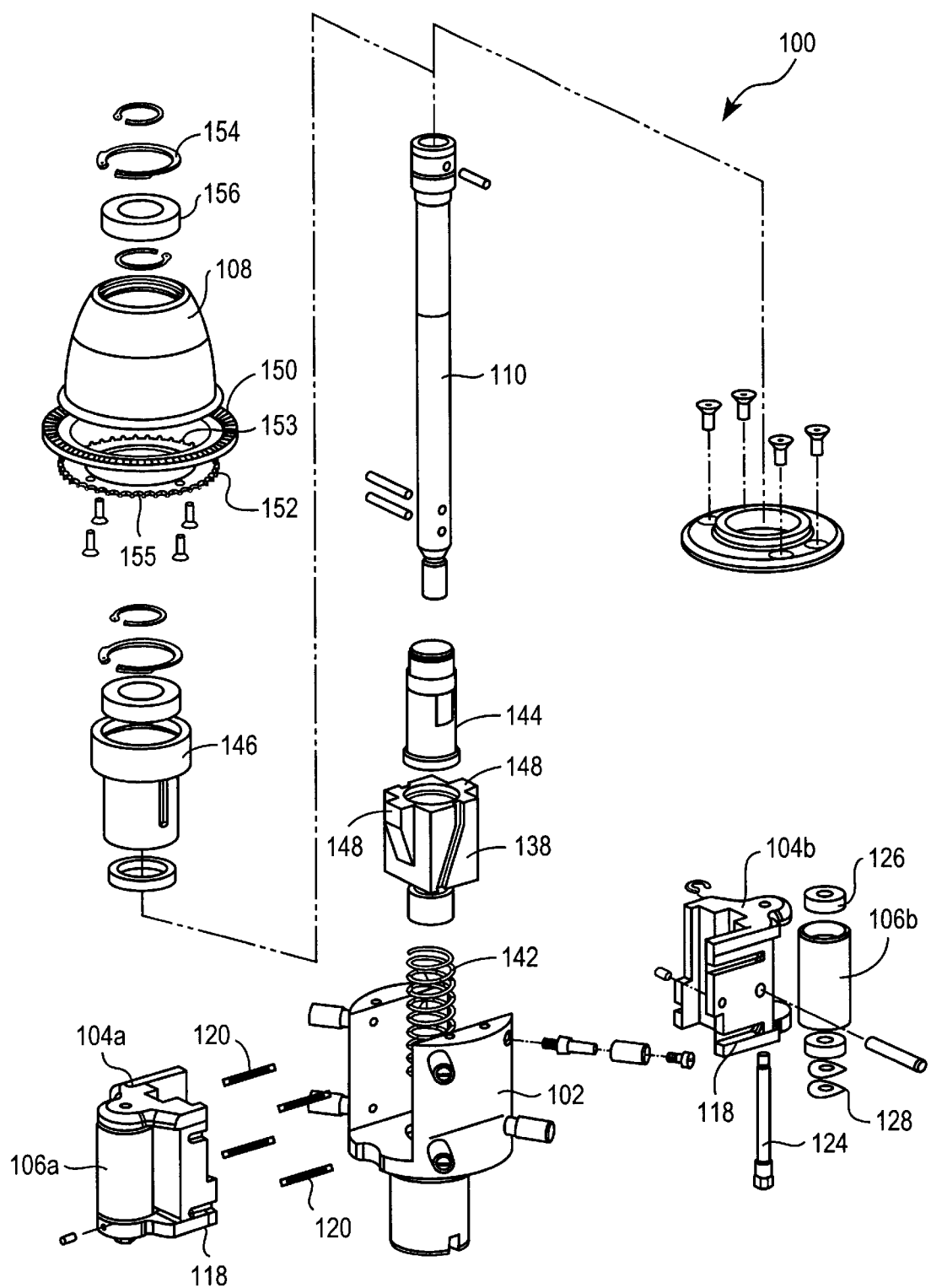
FIG. 3 is an exploded view of a peristaltic pump according to the present invention.

A peristaltic pump rotor assembly according to the present invention is shown generally by reference numeral 100 in the exploded view of FIG. 3. Rotor assembly 100 includes a pump or rotor hub 102, at least one and preferably two opposing roller slides 104a, 104b, a roller 106a, 106b disposed within each roller slide, respectively, and an adjustment knob 108 for adjusting the occlusion of the flexible tube within the pump housing. The rotor assembly 100 is rotatably supported within a stator similar to that shown in FIG. 1 and as known in the art, and the inner circumferential surface of the stator forms the raceway for the rollers 106a, 106b of the present invention. A main shaft 110 extending through the rotor assembly 100 rotates according to the rotation of a drive shaft, which is rotated by a conventional drive mechanism, as shown in FIG. 1, for example.

Each of the roller slides 104a, 104b includes a plurality of recesses or channels 118 for receiving an extension spring 120. Each of the channels 118 includes, preferably at an outer end thereof, a peg to which the opposing ends of the springs are attached. As such, the opposing roller slides 104a and 104b are interconnected by a plurality of springs 120. The rollers 106a, 106b are firmly held in the proper position within the roller slides 104a, 104b, respectively, by a roller shaft 124. Various bearings 126 and washers 128 may also be used for mounting the rollers 106a, 106b within the roller slides 104a, 104b, respectively.

As shown in the illustrated embodiment, the rotor assembly 100 further includes a cam block 138 which is spring loaded by a spring 142. A guide collar 144 engages an upper surface of the cam block 138 and vertically adjusts the position of cam block 138 through rotation of the adjustment knob 108 and a screw adjustment member 146 which rotates therewith and thereby correspondingly rotates the guide collar 144. The cam block 138 includes opposing wedge-shaped projections 148 which engage a corresponding wedge-shaped surface (not shown) on an inner surface of each roller slide 104a, 104b. Thus, as the adjustment knob 108 is rotated clockwise, for example, and screw adjustment member 146 correspondingly rotates so as to move guide collar 144 in a downward direction, cam block 138 is also moved downward such that the wedge projections 148 on the cam block 138 force the roller slides 104a, 104b radially outward against the force of extension springs 120.

The adjustment knob 108 also includes an occlusion indicator ring 150 and a detent ring 152 for providing an audible indication of the degree of rotation of the knob 108. As shown, the detent ring 152 preferably has a scalloped periphery defining a plurality of teeth 153 with generally U-shaped cut-outs 155 therebetween. A plurality of retaining rings 154 and bearings 156 may also be provided.

Whereas the prior art included a continuously applied brake to prevent backlash of the rollers 106a, 106b, the present invention employs an intelligent, momentarily applied dynamic brake, rather than a continuously applied brake. This momentary dynamic brake avoids backlash, due to counter rotation, and in addition, it does not preclude the option of hand operating the roller pump. The dynamic brake achieves this by initiating the braking operation after the pump is requested to stop, and only after the roller pump has decelerated below a predefined speed (e.g., 20 rpm). Moreover, the dynamic brake provides braking for only a very brief duration. It is advantageous to initiate braking after the pump has decelerated below this predefined speed because it prevents abrupt deceleration and mechanical shock to the system.

Figure 4:
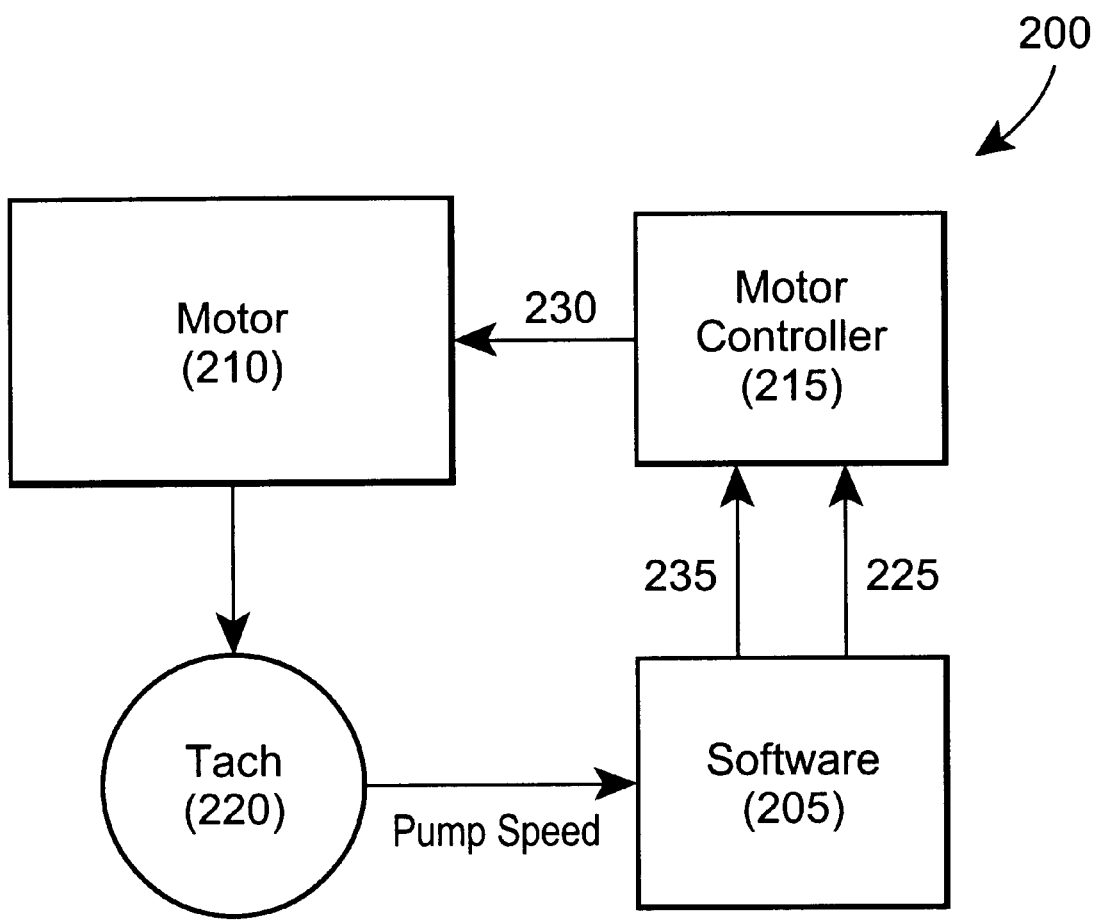
FIG. 4 is a block diagram of a preferred embodiment of the dynamic brake and backlash control system of the present invention.

FIG. 4 is a block diagram of the dynamic brake and backlash control system 200, in accordance with a preferred embodiment of the present invention. As shown, the system involves software 205, a motor 210 (e.g., a 3-phase brushless motor, though it will be understood that the dynamic braking operation of the present invention is also applicable to brush motors), where the motor 210 drives the pump's rollers, a motor controller 215 and a tachometer 220. The software 205, which controls the dynamic braking process, is stored in a memory which is preferably located in the roller pump. In general, the software 205 controls the momentary dynamic braking process by monitoring the speed of the roller pump based on the output of the tachometer 220. When the software 205 determines that it is appropriate to employ the momentary dynamic brake, for example, when the software 205 determines that the pump has been requested to stop and that the speed of the roller pump has dropped below a predetermined pump speed threshold, the software 205 issues a first instruction 225 for the motor controller 215 to activate a control signal 230, where the activation of the control signal 230 activates the dynamic brake. If the motor is a 3-phase motor, the control signal 230 may activate the dynamic brake by simultaneously turning on all three phases of the 3-phase motor. This effectively results in shorting the motor windings, which in turn, provides a braking torque that is dependent on motor speed. However, the software 205 only permits dynamic braking for a relatively short, predetermined time period, which is only long enough for the fluid pressure in the fluid conduit to subside. After this relatively short time duration expires, the software 205 issues a second instruction 235 for the motor controller 215 to deactivate the control signal 230 which releases the dynamic brake. Upon releasing the dynamic brake, the rollers can rotate freely and the roller pump may be hand-operated. In the event of a fault condition, where the dynamic brake is not released, it is still possible to hand-operate the pump.

Figure 5:
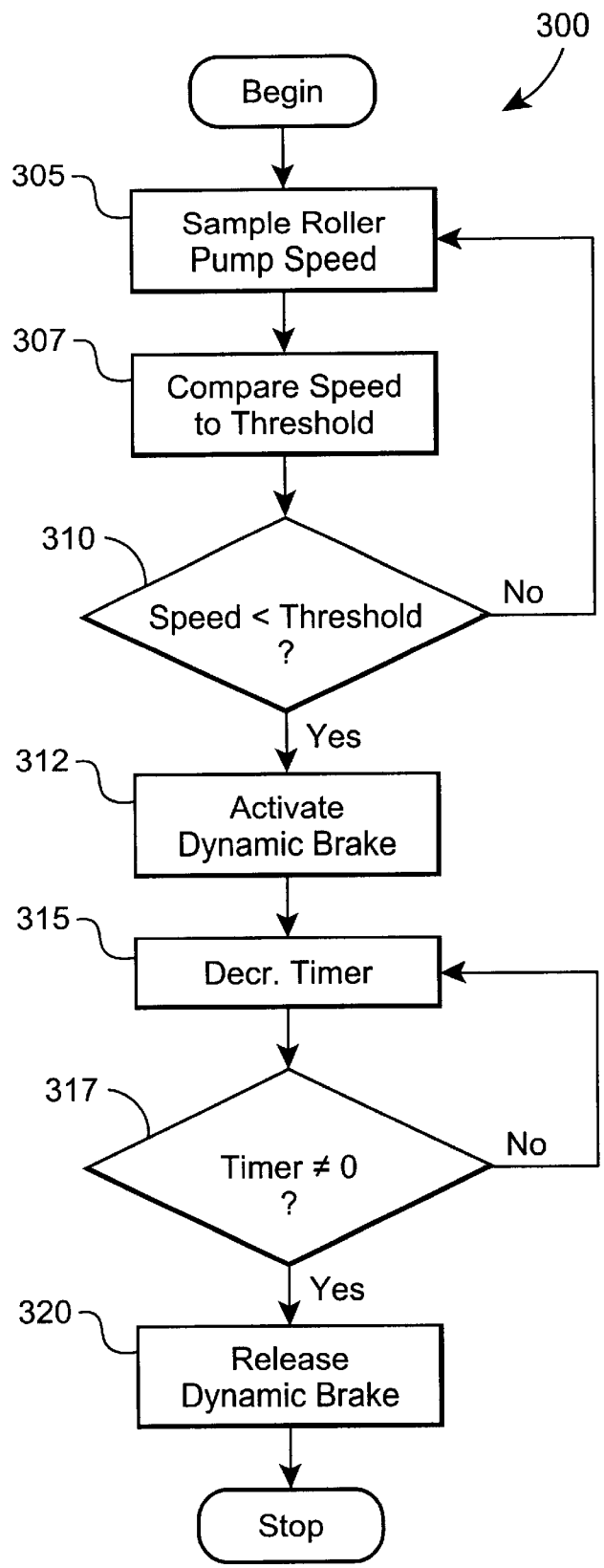
FIG. 5 is a flow chart of an exemplary process through which software may control dynamic braking.

FIG. 5 is a flow chart depicting an exemplary process 300 through which the software 205 may control momentary dynamic braking. The software 205 begins the process upon receiving an indication that the pump shall be stopped. When this occurs, the software 205, as shown in step 305, begins sampling the speed of the roller pump (e.g., by sampling the output of the tachometer 220). The software 205 then compares the sampled pump speed to a predefined pump speed threshold (e.g., 20 rpm) according to step 307. If, based on this comparison, the software 205 determines that the sampled pump speed has not dropped below this threshold, in accordance with the "NO" path out of decision step 310, the software 205 returns to step 305 and takes another pump speed sample.

The software 205 continues to sample the pump speed and compare it to the predefined threshold until it has determined that the pump speed drops below the threshold, in accordance with the "YES" path out of decision step 310. When the software 205 has made this determination, it instructs the motor controller 215 to engage the dynamic brake. Again, if the motor is a 3-phase motor, this may involve activating all three phases of the 3-phase motor 210, as indicated by step 312.

When the motor controller 215 engages the dynamic brake, the software 205 begins decrementing a timer in accordance with step 315. The software 205 then determines whether the timer has decremented to zero, as shown by decision step 317. If, according to the "NO" path out of decision step 320, the timer has not yet decremented to zero, the software 205 once again decrements the timer according to step 315. The software 205 continues to decrement the timer and, after doing so, determine whether the timer has reached zero. When it does determine that the timer has decremented to zero, in accordance with the "YES" path out of decision step 317, the software 205 instructs the motor controller 215 to send the appropriate signal to the motor releasing the dynamic brake, as shown by step 320. The period of time associated with the timer should be sufficiently long to allow the fluid pressure in the conduit to subside. In a preferred embodiment of the present invention, this may be approximately 2 seconds, plus or minus 1 second.

While the above described dynamic brake has been illustrated with respect to a preferred embodiment and use within a peristaltic pump, it should be apparent to one skilled in the art that the applications of the momentary dynamic brake extend further to other devices and situations within the scope of the present invention.

Further, while the present invention has been described with preferred embodiments, it is to be understood that variations and modifications may be resorted to as will be apparent to those skilled in the art. Such variations and modifications are to be considered within the purview and the scope of the present invention.

What is claimed is:

1. A roller pump comprising:
   a fluid conduit;
   means for activating a dynamic brake when the roller pump decelerates below a predefined pump speed; and
   means for deactivating the dynamic brake when pressure in the fluid conduit subsides.

2. The roller pump of claim 1 further comprising:
   means for determining when the roller pump decelerates below the predefined pump speed.

3. The roller pump of claim 2, wherein said means for determining when the roller pump decelerates below the predefined pump speed comprises:
   a tachometer for measuring roller pump speed; and
   means for comparing measured roller pump speed to the predefined pump speed.

4. The roller pump of claim 1 further comprising:
   a motor; and
   control means for shorting the windings in the motor.

5. The roller pump of claim 1 further comprising an electric motor wherein said means for deactivating the dynamic brake when pressure in the fluid conduit subsides comprises:
   means for determining whether a predefined period of time has elapsed; and
   means for deactivating all phases of the electric motor when the time period has elapsed, wherein the predefined period of time represents a period of time required for the pressure in the fluid conduit to subside.

6. In a roller pump, a method for preventing backlash comprising the steps of:
   during deceleration of the roller pump, determining whether the speed of the roller pump is less than a predefined roller pump speed threshold;
   when it has been determined that the speed of the roller pump is less than the predefined roller pump speed threshold, activating a dynamic brake; and
   deactivating the dynamic brake after a predefined period of time has elapsed.

7. The method of claim 6, wherein said step of determining whether the speed of the roller pump is less than a predefined roller pump speed threshold comprises the steps of:
   measuring roller pump speed; and
   comparing measured roller pump speed to the predefined roller pump speed threshold.

8. The method of claim 6, wherein said step of activating a dynamic brake comprises the step of:
   shorting the windings of a motor in the roller pump.

9. The method of claim 6, wherein said step of deactivating the dynamic brake after a predefined period of time has elapsed comprises the step of:
   deactivating all phases of an electric motor in the roller pump.

10. The method of claim 6 further comprising the steps of:
    initiating a timer which reflects an amount of time equal to the predefined period of time; and
    decrementing the timer until it indicates that the predefined period of time has elapsed, wherein the predefined period of time represents a period of time required for pressure in a fluid conduit associated with the roller pump to subside.

* * * * *